United States Patent
Ishibashi et al.

(10) Patent No.: US 6,936,709 B2
(45) Date of Patent: Aug. 30, 2005

(54) METHOD FOR PURIFYING PROTECTED 2'-DEOXYCYTIDINES AND HYDRATED CRYSTALS THEREOF

(75) Inventors: Hiroki Ishibashi, Omuta (JP); Kiyoteru Nagahara, Omuta (JP); Yasushi Fukuiri, Omuta (JP); Yasuko Matsuba, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/453,481

(22) Filed: Jun. 4, 2003

(65) Prior Publication Data

US 2003/0229223 A1 Dec. 11, 2003

(30) Foreign Application Priority Data

Jun. 5, 2002 (JP) ........................................ 2002-163889

(51) Int. Cl.[7] .............................................. C07H 19/048
(52) U.S. Cl. ................. 536/28.5; 536/23.1; 536/25.34; 536/25.31; 536/25.3; 536/25.4; 536/26.8; 536/28.51; 536/22.1; 546/44; 530/330; 514/203; 514/49
(58) Field of Search .............................. 536/28.5, 23.1, 536/25.34, 25.31, 25.3, 25.4, 26.8, 28.51, 22.1; 546/44; 530/330; 514/203, 49

(56) References Cited

U.S. PATENT DOCUMENTS

| | | |
|---|---|---|
| 4,973,679 A | 11/1990 | Caruthers et al. |
| 5,179,200 A * | 1/1993 | Molko et al. ............... 536/26.8 |

FOREIGN PATENT DOCUMENTS

| | | |
|---|---|---|
| EP | 0 090 789 A1 | 5/1983 |
| JP | 58-180500 | 10/1983 |
| JP | 60-152495 | 8/1985 |
| JP | 63-179889 | 7/1988 |
| JP | 6-507883 | 9/1994 |
| WO | 92/13869 | 8/1992 |
| WO | 00/39138 A1 | 7/2000 |
| WO | 00/75154 A2 | 12/2000 |

* cited by examiner

*Primary Examiner*—James O. Wilson
*Assistant Examiner*—Devesh Khare
(74) *Attorney, Agent, or Firm*—Burns, Doane, Swecker & Mathis, LLP

(57) ABSTRACT

A protected 2'-deoxycytidine is purified by precipitating the protected 2'-deoxycytidine represented by general formula (3) in the form of a hydrated crystal from a solution containing the protected 2'-deoxycytidine and water, and by recovering the protected 2'-deoxycytidine:

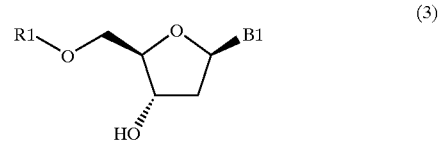

(3)

wherein R1 represents a 4-methoxytrityl, 4,4'-dimethoxytrityl, or triphenylmethyl group; and B1 represents a cytosine group having a protected amino group. The compound represented by general formula (3) is, in particular, a protected 2'-deoxycytidine represented by formula (4):

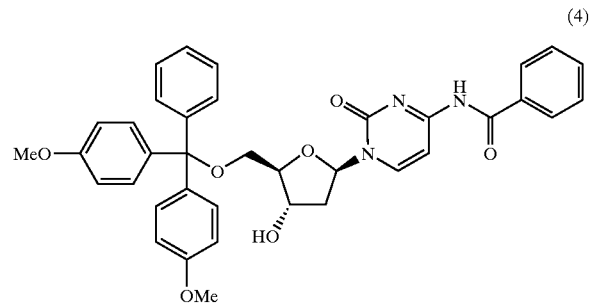

(4)

The 2'-deoxycytidine is used as a raw material for antisense DNA.

2 Claims, No Drawings

METHOD FOR PURIFYING PROTECTED 2'-DEOXYCYTIDINES AND HYDRATED CRYSTALS THEREOF

BACKGROUND OF THE INVENTION

1. Field of the Invention

The present invention relates to protected 2'-deoxycytidines and hydrated crystals thereof and, particularly, to a method for producing and purifying 5' position-protected 2'-deoxycytidines.

The 5' position-protected 2'-deoxycytidines are useful compounds as raw materials for antisense DNA, which have been developed in recent years.

2. Description of the Related Art

Recently, antisense DNA drugs have been intensively developed with progress in the development of genomic medicines. The progress has raised demands for DNA oligomers, the raw materials for antisense DNA drugs, and protected deoxynucleosides, the raw materials for DNA oligomers. On the other hand, applications for producing medicines require the use of extremely high-purity intermediate products to minimize the generation of byproducts attributed to impurities.

Japanese Unexamined Patent Application Publication Nos. 58-180500 and 63-179889 and PCT Japanese Translation Patent Publication No. 06-507883 disclose that 5' position-protected deoxynucleosides can be purified by column chromatography. This method can relatively easily remove impurities having largely different polarities and structures, but cannot satisfactorily remove impurities having similar structures. For example, it is particularly difficult to remove impurities having 5'- and 3'-hydroxyl groups protected by trityl derivatives such as dimethoxytrityl groups, and those having an unrequired 3'-hydroxyl group, instead of a required 5'-hydroxyl group, protected by a trityl derivative such as a dimethoxytrityl group. In addition, a mixture of these impurities significantly affects the subsequent steps in the production of medicines. Furthermore, column chromatography involves a large-scale purifying apparatus and a large amount of solvent in industrial production; hence, this method will be unsuitable for mass production of large quantities of product in the future.

Methods other than column chromatography for removing impurities have been studied. Specifically, purification by reprecipitation is disclosed in Japanese Unexamined Patent Application Publication No. 60-152495 and PCT Publication Nos. WO00/75154 and WO00/39138. In the reprecipitation method, a poor solvent is added to a good solvent containing a crude compound or the good solvent containing a crude compound is added dropwise to the poor solvent to precipitate the target substance. This method, therefore, has a low purification ability in principle, causing difficulty in removing the impurities described above. In addition, it is difficult to appropriately control the volume ratio between the good and poor solvents in industrial production. An inappropriate ratio generates an oily or viscous precipitate. As a result, purification is often unsuccessful. In fact, according to a method disclosed in Japanese Unexamined Patent Application Publication No. 60-152495, the reprecipitation process produces the target substance in the form of a viscous liquid, which is unsuitable for industrial applications. Methods for amorphization by reprecipitation have been disclosed, but no method for generating a crystal by crystallization is known.

SUMMARY OF THE INVENTION

Accordingly, it is an object of the present invention to provide a method for the effective manufacture of high-purity protected 2'-deoxycytidines without requiring special equipment.

As a result of intensive study for achieving the object, the present inventors successfully prepared a hydrated crystal of a protected 2'-deoxycytidine from a solution containing the protected 2'-deoxycytidine and water, and found that purification by crystallization or recrystallization, which was difficult for the conventional art, could be achieved.

The present invention, therefore, provides a hydrated crystal of a protected 2'-deoxycytidine represented by general formula (1):

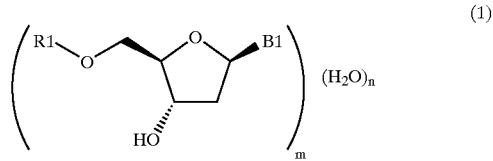

wherein each of m and n represents an integer; R1 represents a 4-methoxytrityl, 4, 4'-dimethoxytrityl, or triphenylmethyl group; and B1 represents a cytosine group having a protected amino group.

The compound represented by general formula (1) is preferably a protected 2'-deoxycytidine represented by general formula (2):

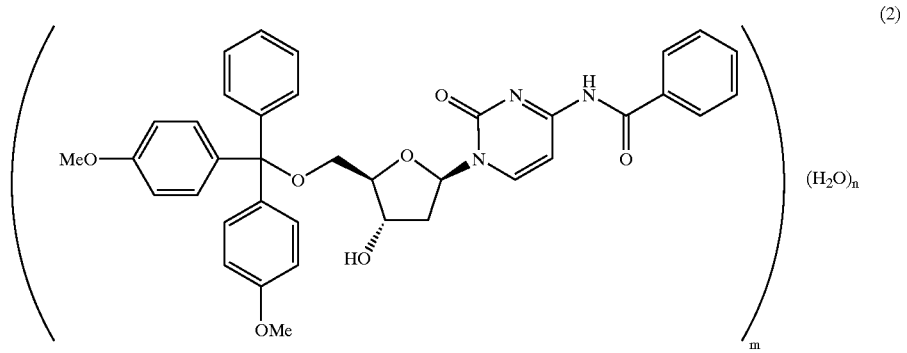

wherein m and n are as defined above.

In the hydrated crystal, the content of $N^4$-benzoyl-3'-O-(4, 4'-dimethoxytrityl)-2'-deoxycytidine is preferably 0.1% or less.

The present invention further provides a method for purifying a protected 2'-deoxycytidine by precipitating the protected 2'-deoxycytidine represented by general formula (3) in the form of a hydrated crystal from a solution containing the protected 2'-deoxycytidine and water, and recovering the protected 2'-deoxycytidine:

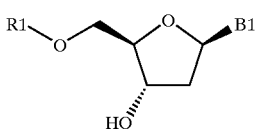

wherein R1 and B1 are as defined above.

In this method, the content of water in the solution is preferably 0.5 or more equivalents of the compound represented by general formula (3).

In this method, the compound represented by general formula (3) is preferably a protected 2'-deoxycytidine represented by formula (4):

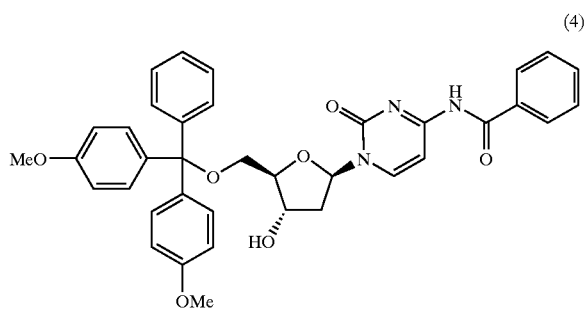

In the method, the content of $N^4$-benzoyl-3'-O-(4,4'-dimethoxytrityl)-2'-deoxycytidine in the purified crystal is preferably 0.1% or less.

The present invention further provides a method for producing an unhydrated protected 2'-deoxycytidine represented by general formula (3) or formula (4) by dehydrating the hydrated crystal of a protected 2'-deoxycytidine represented by general formula (1) or (2) at a reduced pressure.

The method of the present invention allows more effective manufacturing of high-purity protected 2'-deoxycytidines on an industrial scale.

DESCRIPTION OF THE PREFERRED EMBODIMENTS

The present invention will now be described in detail.

In general formulas (1) and (3) according to the present invention, B1 represents a cytosine group having an amino group protected by a protective group. Examples of the protective group include an alkyl group, an alkylacyl group, and a benzoyl group that may be substituted.

The alkyl group may be linear or branched, and may have another functional group (substituent). Examples of the substituent include methyl, ethyl, n-propyl, 2-propyl, n-butyl, and iso-butyl groups.

The alkylacyl group may be linear, branched, or ringed, and may have another functional group (substituent). Examples of the substituents include acetyl, propionyl, n-butyryl, iso-butyryl, pivaloyl, valeryl, isovaleryl, cyclopropyl, phenylacetyl, phenoxyacetyl, and (isopropylphenoxy)acetyl groups.

The benzoyl group may be substituted. The phenyl group in the benzoyl group may have a substituent either at a 2, 3, or 4 position, or a plurality of substituents at these positions. Examples of the substituent include alkyl groups such as methyl, ethyl, 2-propyl, n-butyl, and tert-butyl groups; hydroxyl groups; alkyloxy groups such as methoxy, ethoxy, n-propyloxy, 2-propyloxy, and n-butyloxy groups; nitro groups; halogen groups such as fluoro, chloro, bromo, and iodo groups; amino groups; alkylamino groups such as methylamino, ethylamino, n-propylamino, dimethylamino, diethylamino, and diisopropylamino groups; acyl groups such as acetyl, propionyl, and benzoyl groups; phenyl groups; and pyridinyl groups.

Specifically, examples of the benzoyl groups include benzoyl, 2-chlorobenzoyl, 3-chlorobenzoyl, 4-chlorobenzoyl, 2-bromobenzoyl, 3-bromobenzoyl, 4-bromobenzoyl, 2-fluorobenzoyl, 3-fluorobenzoyl, 4-fluorobenzoyl, 2-methoxybenzoyl, 3-methoxybenzoyl, 4-methoxybenzoyl, 2-nitrobenzoyl, 3-nitrobenzoyl, 4-nitrobenzoyl, 2-aminobenzoyl, 3-aminobenzoyl, 4-aminobenzoyl, 2-methylaminobenzoyl, 3-methylaminobenzoyl, 4-methylaminobenzoyl, 2-dimethylaminobenzoyl, 3-dimethylaminobenzoyl, 4-dimethylaminobenzoyl, 4-phenylbenzoyl, and 4-acetylbenzoyl groups.

A solution containing protected 2'-deoxycytidines and water may further contain another miscible solvent that can precipitate hydrated crystals of the protected 2'-deoxycytidines. Examples of nonaqueous solvents include alcohols such as methanol, ethanol, propanol, isopropyl alcohol, butanol, pentanol, and cyclohexanol; ethers such as diethyl ether, tetrahydrofuran, and dioxane; ketones such as acetone, methyl ethyl ketone, and methyl isobutyl ketone; saturated hydrocarbons such as pentane, hexane, methylpentane, cyclohexane, heptane, nonane, and decane; aromatic hydrocarbons such as benzene, toluene, cumene, xylene, mesitylene, diisopropylbenzene, and triisopropylbenzene; halogenated hydrocarbons such as dichloromethane, chloroform, and dichloroethane; pyridines such as pyridine, lutidine, and quinoline; and polar solvents such as tertiary amines (e.g. triethylamine and tributylamine), acetonitrile, dimethylformamide, dimethylimidazolidinone, and dimethylsulfoxide. These solvents may be used alone or in combinations.

In the hydrated crystals, water facilitates the formation of a crystal structure. The hydrated crystals in the present invention include crystals incorporating water in the crystal lattice and compound crystals formed by weak interaction between the protected 2'-deoxycytidines and water. The form of the hydrated crystals and the crystal structure are not limited.

The hydrated crystals of the protected 2'-deoxycytidines may contain a small amount of the nonaqueous solvent contained in the aqueous protected 2'-deoxycytidine solution during the crystallization process.

The content of water used in the crystallization may be 0.5 equivalents or more, and preferably 1.0 equivalent or more, of the protected 2'-deoxycytidines.

Methods of forming the hydrated crystals are not limited in the present invention. For example, the crystals can be formed by adding water to a solution containing the protected 2'-deoxycytidines or by adding the protected 2'-deoxycytidines to an aqueous solvent.

The concentration of the protected 2'-deoxycytidines in the crystallization usually ranges from 1% to 50%, and preferably from 5% to 40%.

The temperature of the solution during the crystallization preferably ranges from −10° C. to the boiling point of the solvent, although the temperature is not limited to this range. A single crystallization step usually ensures satisfactorily high purity; however, a further crystallization step provides higher purity. Seed crystals may be used for facilitating the crystallization.

The hydrated crystals of the protected 2'-deoxycytidines purified in such a manner may be dehydrated, if necessary, at a reduced pressure, preferably in the range of 0.1 to 100 mmHg, forming hydrated protected 2'-deoxycytidine crystals with a reduced water content, unhydrated protected 2'-deoxycytidine powder, or partially hydrated protected 2'-deoxycytidine powder.

The dehydration temperature is not limited and usually ranges from room temperature to 200° C. The dehydration can be performed with a flowing dry gas (e.g. nitrogen) or a dehydrating agent (e.g. silica gel and diphosphorus pentoxide).

Impurities removable by the purifying method according to the present invention include $N^4$-benzoyl-3'-O-(4, 4'-dimethoxytrityl)-2'-deoxycytidine and $N^4$-benzoyl-3', 5'-O-bis(4, 4'-dimethoxytrityl)-2'-deoxycytidine. The content of the $N^4$-benzoyl-3'-O-(4, 4'-dimethoxytrityl)-2'-deoxycytidine in the protected 2'-deoxycytidines is 0.1% or less, and preferably 0.01% or less, regardless of whether the hydrated crystal remains. The content of the $N^4$-benzoyl-3', 5'-O-bis(4, 4'-dimethoxytrityl)-2'-deoxycytidine in the protected 2'-deoxycytidines is 0.3% or less, and preferably 0.1% or less, regardless of whether the hydrated crystal remains (where the percentages are expressed as percent area as measured by liquid chromatography).

As described above, the present invention provides efficient purification of the protected 2'-deoxycytidines.

The following examples describing the present invention do not serve to limit the scope of the invention in any way.

EXAMPLES

Condition 1 for High Performance Liquid Chromatography (HPLC) for Examples and Comparative Examples
(Analytical Condition for $N^4$-benzoyl-2'-deoxycytidine and $N^4$-benzoly-3', 5'-O-bis(4, 4'-dimethoxytrityl)-2'-deoxycytidine)
Column: Develosil TMS-UG-5
  150 mm×4.6 mm in diameter
Flow rate: 0.6 mL/min.
Column temperature: 35° C.
Detection wavelength: 254 nm
Mobile phase: gradients

| Time (min.) | Solution B (%) |
| --- | --- |
| 0 | 20 |
| 30 | 100 |
| 35 | 100 |
| 37 | 20 |
| 50 | END |

[Solution A]
Methanol (60 mL) was mixed to a solution of $NaH_2PO_4.2H_2O$ (1.92 g) and $Na_2HPO_4$ (2.43 g) in water (2,940 mL), and the mixture was deaerated.
[Solution B]
Methanol (2,700 mL) was mixed to a solution of $NaH_2PO_4.2H_2O$ (196 mg) and $Na_2HPO_4$ (248 mg) in water (300 mL), and the mixture was deaerated.
Condition 2 for HPLC for Examples and Comparative Examples
(Analytical Condition for $N^4$-benzoyl-3'-O-(4, 4'-dimethoxytrityl)-2'-deoxycytidine)
Column: YMC-Pack CN A-512
  150 mm×6.0 mm in diameter
Flow rate: 1.0 mL/min.
Column temperature: 35° C.
Detection wavelength: 235 nm
Run time: 80 min.
Injection volume: 10 μL
Mobile phase: gradients

| Time (min.) | Solution B (%) |
| --- | --- |
| 0 | 14 |
| 25 | 50 |
| 60 | 100 |
| 80 | 100 |
| 82 | 14 |
| 102 | END |

[Solution A]
A solution of $NH_4H_2PO_4$ (1.15 g) and $(NH_4)_2HPO_4$ (0.92 g) in water (2,000 mL) was deaerated.
[Solution B]
A mixture of acetonitrile (1,200 mL) and Solution A (400 mL) was deaerated.
Conditions for X-ray Diffractometry (XRD) for Examples and Comparative Examples
Apparatus: RAD-1A (Rigaku International Corporation)
X-ray target: Cu, 30 kV 15 mA
Scanning rate: 2°/min.
Conditions for Differential Scanning Calorimetry (DSC) for Examples and Comparative Examples
Apparatus: DSC821e (METTLER TOLEDO)
DSC pan: aluminum
Heating rate: 5° C./min.
Atmosphere: $N_2$ stream

Reference Example 1

Preparation of $N^4$-benzoyl-5'-O-(4, 4'-dimethoxytrityl)-2'-deoxycytidine

To a solution of $N^4$-benzoyl-2'-deoxycytidine (119.0 g) in pyridine (1.5 L), 4, 4'-dimethoxytritylchloride (113.5 g) was added over two hours and the mixture was stirred at room temperature for a further four hours. Sodium hydrogencarbonate (33.8 g) was added and stirred for two hours, and then the reaction solution was condensed. Ethyl acetate (1.2 L) and water (300 mL) were added to the residue and the mixture was stirred. A small amount of saturated saline solution was added to the mixture and the resultant liquid was separated. The extracted organic layer was washed with water, and dried with anhydrous magnesium sulfate. The mixture was filtered and then the solvent was removed. The residue was purified by silica gel column chromatography with ethyl acetate as a solvent. A fraction including the target substance was added dropwise to diisopropyl ether (2.0 L) with vigorous stirring, and then the resultant mixture was stirred at room temperature for two hours. The filtrate was dried in a vacuum at 50° C. to yield non-hydrated $N^4$-benzoyl-5'-O-(4, 4'-dimethoxytrityl)-2'-deoxycytidine (153.3 g). The XRD pattern showed that the free product was amorphous. Furthermore, the component contained $N^4$-benzoyl-2-deoxycytidine, which was the raw material, $N^4$-benzoyl-3'-O-(4, 4'-dimethoxytrityl)-2'-deoxycytidine, and $N^4$-benzoyl-3', 5'-O-bis(4, 4'-dimethoxytrityl)-2'-deoxycytidine, both of which were byproducts, and the rates of the respective peak areas were 1.0%, 0.15%, and 2.2%, respectively.

Example 1

Synthesis of Hydrated Crystals of $N^4$-benzoyl-5'-O-(4, 4'-dimethoxytrityl)-2'-deoxycytidine The non-hydrated $N^4$-benzoyl-5'-O-(4, 4'-dimethoxytrityl)-2'-deoxycytidine (2.0 g), which was prepared in Reference Example 1, was dissolved in 1,2-dichloroethane (5 mL) and water (0.1 g) was added to the solution. The solution was allowed to stand at −24° C. for one day to crystallize the target substance. The resultant crystals were filtered and dried in a vacuum at 50° C. to yield hydrated crystals of $N^4$-benzoyl-5'-O-(4, 4'-dimethoxytrityl)-2'-deoxycytidine (0.8 g). The moisture content in the crystals, as measured by the Karl Fischer method, was 2.7%. The XRD pattern had distinct peaks assigned to the crystals in particular at 5.6°, 70°, and 10.3°. Moreover, the DSC thermogram had an endothermic peak at 109° C. indicating the melting point of the crystals.

The component contained $N^4$-benzoyl-2'-deoxycytidine, $N^4$-benzoyl-3'-O-(4, 4'-dimethoxytrityl)-2'-deoxycytidine, and $N^4$-benzoyl-3', 5'-O-bis(4, 4'-dimethoxytrityl)-2'-deoxycytidine, and the rates of respective peak areas were 0.05%, the detection limit (0.01%) or less, and 0.05%, respectively.

$^1$H NMR (CDCl$_3$): δ 8.7 (s,1H); 8.3 (d,1H); 7.9 (d,2H); 7.2–7.6 (m,13H); 6.8–6.9 (m,4H); 6.3 (m,1H); 4.5 (m,1H); 4.2 (m,1H); 3.8 (s,6H); 3.4–3.5 (m,2H); 2.7–2.9 (m,2H); 2.3 (m,1H)

Example 2

Synthesis of Hydrated Crystals of $N^4$-benzoyl-5'-O-(4, 4'-dimethoxytrityl)-2'-deoxycytidine The non-hydrated $N^4$-benzoyl-5'-O-(4, 4'-dimethoxytrityl)-2'-deoxycytidine (2.0 g), which was prepared in Reference Example 1, was dissolved in butyl acetate (5 mL). Hexane (0.5 mL) was added dropwise to the solution. Then water (0.1 g) and the hydrated crystals of $N^4$-benzoyl-5'-O-(4, 4'-dimethoxytrityl)-2'-deoxycytidine (10 mg), which were prepared in Example 1, were added to the solution and the mixture was allowed to stand on ice for one day to crystallize the target substance. The resultant crystals were filtered and dried in a vacuum at 50° C. to yield hydrated crystals of $N^4$-benzoyl-5'-O-(4, 4'-dimethoxytrityl)-2'-deoxycytidine (1.3 g). The moisture content of the crystals, as measured by the Karl Fischer method, was 2.2%. The XRD pattern had distinct peaks assigned to the crystals, in particular at 5.6°, 7°, and 10.3°. Moreover, the DSC thermogram had an endothermic peak at 112° C. indicating the melting point of the crystals.

The component contained $N^4$-benzoyl-2'-deoxycytidine, $N^4$-benzoyl-3'-O-(4, 4'-dimethoxytrityl)-2deoxycytidine, and $N^4$-benzoyl-3', 5'-O-bis(4, 4'-dimethoxytrityl)-2'-deoxycytidine, and the rate of the respective peak areas were 0.12%, the detection limit (0.01%) or less, and 0.07%, respectively.

Example 3

Synthesis of Hydrated Crystals of $N^4$-benzoyl-5'-O-(4, 4'-dimethoxytrityl)-2'-deoxycytidine The non-hydrated $N^4$-benzoyl-5'-O-(4, 4'-dimethoxytrityl)-2'-deoxycytidine (2.0 g), which was prepared in Reference Example 1, was dissolved in acetonitrile (5 mL). Water (7 mL) was added dropwise to the solution. Then the hydrated crystals of $N^4$-benzoyl-5'-O-(4, 4'-dimethoxytrityl)-2'-deoxycytidine (10 mg), which were prepared in Example 1, were added to the solution and the mixture was allowed to stand on ice for five hours to crystallize the target substance. The resultant crystals were filtered and dried in a vacuum at 50° C. to yield hydrated crystals of $N^4$-benzoyl-5'-O-(4, 4'-dimethoxytrityl)-2'-deoxycytidine (1.3 g). The DSC thermogram had an endothermic peak at 112° C. indicating the melting point of the crystals.

The component contained $N^4$-benzoyl-2'-deoxycytidine, $N^4$-benzoyl-3'-O-(4, 4'-dimethoxytrityl)-2-deoxycytidine, and $N^4$-benzoyl-3', 5'-O-bis(4, 4'-dimethoxytrityl)-2'-deoxycytidine, and the rates of the respective peak areas were 0.1%, the detection limit (0.01%) or less, and 0.04%, respectively.

Example 4

Synthesis of Hydrated Crystals of $N^4$-benzoyl-5'-O-(4, 4'-dimethoxytrityl)-2'-deoxycytidine The non-hydrated $N^4$-benzoyl-5'-O-(4, 4'-dimethoxytrityl)-2'-deoxycytidine (2.0 g), which was prepared in Reference Example 1, was dissolved in acetone (5 mL). Water (8 mL) was added dropwise to the solution. Then the hydrated crystals of $N^4$-benzoyl-5'-O-(4, 4'-dimethoxytrityl)-2'-deoxycytidine (10 mg), which were prepared in Example 1, ware added to the solution and the mixture was allowed to stand on ice for five hours to crystallize the target substance. The resultant crystals were filtered and dried in a vacuum at 50° C. to yield hydrated crystals of $N^4$-benzoyl-5'-O-(4, 4'-dimethoxytrityl)-2'-deoxycytidine (1.4 g). The DSC thermogram had an endothermic peak at 114° C. indicating the melting point of the crystals.

The component contained $N^4$-benzoyl-2'-deoxycytidine, $N^4$-benzoyl-3'-O-(4, 4'-dimethoxytrityl)-2deoxycytidine, and $N^4$-benzoyl-3', 5'-O-bis(4, 4'-dimethoxytrityl)-2'-deoxycytidine and the rates of the respective peak areas were 0.07%, the detection limit (0.01%) or less, and 0.1%, respectively.

Example 5

Synthesis of Hydrated Crystals of $N^4$-benzoyl-5'-O-(4, 4'-dimethoxytrityl)-2'-deoxycytidine $N^4$-benzoyl-2'-deoxycytidine (40.3 g) was suspended in pyridine (302.4 g) and the suspension was cooled to 10-C. To the suspension, 4, 4'-dimethoxytritylchloride (47.5 g) was added at 10-C., and the mixture was stirred at this temperature for four hours. After completion of the reaction, sodium hydrogencarbonate (12.9 g) was added to the mixture and stirred at room temperature for two hours, and then the reaction liquid was condensed. Butyl acetate (473 g) was added to the residue and the resultant mixture was stirred at room temperature for one hour, and then the insoluble component was filtered. Hexane (140 g) was added dropwise to the resultant organic layer at room temperature. Water (3.3 g) and the hydrated crystals of $N^4$-benzoyl-5'-O-(4, 4'-dimethoxytrityl)-2'-deoxycytidine (0.1 g), which were prepared in Example 1, were added to the organic layer. The mixture was allowed to stand at room temperature for one day to crystallize the target substance and then hexane (93 g) was added dropwise and the crystallization was repeated at room temperature for five hours.

The resultant crystals were filtered and dried in a vacuum at 50° C. to yield hydrated crystals of $N^4$-benzoyl-5'-O-(4, 4'-dimethoxytrityl)-2'-deoxycytidine (63.7 g). The DSC thermogram had an endothermic peak at 110° C. indicating the melting point of the crystals.

The component contained $N^4$-benzoyl-2'-deoxycytidine, $N^4$-benzoyl-3'-O-(4, 4'-dimethoxytrityl)-2'-deoxycytidine, and $^4$-benzoyl-3', 5'-O-bis(4, 4'-dimethoxytrityl)-2'-deoxycytidine and the rates of the respective peak areas were 0.05%, the detection limit (0.01%) or less, and 0.15%, respectively.

Example 6

Purification of Hydrated Crystals of $N^4$-benzoyl-5'-O-(4, 4'-dimethoxytrityl)-2'-deoxycytidine The hydrated crystals of $N^4$-benzoyl-5'-O-(4, 4'-dimethoxytrityl)-2'-deoxycytidine (60 g), which were prepared in Example 5, and active carbon (3 g) were added to acetonitrile (300 g) and the resultant mixture was kept at 55° C. for one hour. The insoluble component was filtered. Water (240 g) was added dropwise and the hydrated crystals of $N^4$-benzoyl-5'-O-(4, 4'-dimethoxytrityl)-2'-deoxycytidine (0.1 g) were added to the solution. The resultant mixture was allowed to stand at room temperature for two hours to crystallize the target substance. Furthermore, water (240 g) was added dropwise and the crystallization was repeated at room temperature for two hours. The resultant crystals were filtered and dried in a vacuum at 50° C. to purify the hydrated crystals of $N^4$-benzoyl-5'-O-(4, 4'-dimethoxytrityl)-2'-deoxycytidine (55.8 g). The moisture content of the crystals, as measured by the Karl Fischer method, was 2.3%.

The DSC thermogram had an endothermic peak at 114° C. indicating the melting point of the crystals.

The component contained $N^4$-benzoyl-2'-deoxycytidine, $N^4$-benzoyl-3'-O-(4, 4'-dimethoxytrityl)-2-deoxycytidine, and $N^4$-benzoyl-3', 5'-O-bis(4, 4'-dimethoxytrityl)-2'-deoxycytidine and the rates of the respective peak areas were the detection limit (0.01%) or less, the detection limit (0.01%) or less, and 0.05%, respectively.

Example 7

Synthesis of Hydrated Crystals of $N^4$-benzoyl-5'-O-(4, 4'-dimethoxytrityl)-2'-deoxycytidine The hydrated crystals of $N^4$-benzoyl-5'-O-(4, 4'-dimethoxytrityl)-2'-deoxycytidine (40 g) were dried with a shelf dryer in a vacuum (10 mmHg) at 65° C. for 40 hours in a nitrogen stream to yield white powdery $N^4$-benzoyl-5'-O-(4, 4'-dimethoxytrityl)-2'-deoxycytidine (39.1 g). The moisture content of the crystals was 0.1%. The XRD pattern had no distinct peak, which indicates that the powder was amorphous. Correspondingly, the DSC thermogram had no endothermic peak.

Comparative Example 1

Referring to PCT Publication No. WO00/75154, the non-hydrated $N^4$-benzoyl-5'-O-(4, 4'-dimethoxytrityl)-2'-deoxycytidine (2.00 g), including $N^4$-benzoyl-2'-deoxycytidine, $N^4$-benzoyl-3'-O-(4, 4'-dimethoxytrityl)-2'-deoxycytidine, and $N^4$-benzoyl-3', 5'-O-bis(4, 4'-dimethoxytrityl)-2'-deoxycytidine with rates by peak areas of 1.0%, 0.15%, and 2.2%, respectively, was dissolved in acetonitrile (2.3 mL). The solution was added dropwise to water (41 mL) with vigorous stirring and the resultant mixture was stirred for one hour. A white precipitate was recovered by filtration, was washed twice with water and was dried at 50° C. in a vacuum to yield $N^4$-benzoyl-5'-O-(4, 4'-dimethoxytrityl)-2'-deoxycytidine (1.82 g). The XRD pattern and the DSC thermogram showed neither an absorption peak nor an endothermic peak due to the crystallization, which indicates the resultant components was not crystallized. Moreover, the component contained $N^4$-benzoyl-2'-deoxycytidine, $N^4$-benzoyl-3'-O-(4, 4'-dimethoxytrityl)-2'-deoxycytidine, and $N^4$-benzoyl-3', 5'-O-bis(4, 4'-dimethoxytrityl)-2'-deoxycytidine and the respective peak areas were 0.9%, 0.13%, and 1.8%, respectively, which indicates that the above procedure had no substantial effect on the purification.

What is claimed is:

1. A hydrated crystal of a protected 2'-deoxycytidine represented by general formula (2):

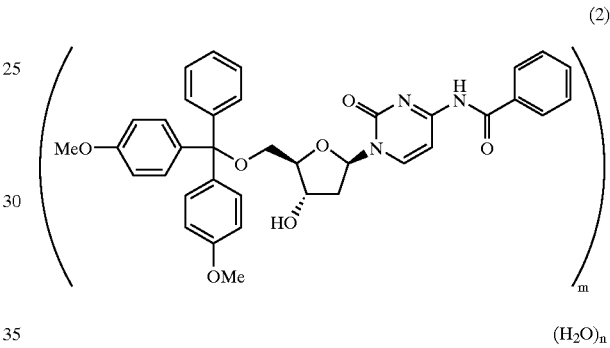

wherein each of m and n are represents an integer.

2. The hydrated crystal according to claim 1 wherein the content of $N^4$-benzoyl-3'-O-(4,4'- dimethoxytrityl)-2'-deoxycytidine is 0.1% or less.

* * * * *